US00PP12672P2

(12) United States Plant Patent
Pouw

(10) Patent No.: US PP12,672 P2
(45) Date of Patent: Jun. 4, 2002

(54) MINIATURE ROSE PLANT NAMED 'RUISKJOL'

(75) Inventor: Antonius A. Pouw, De Kwakel (NL)

(73) Assignee: De Ruiter's Nieuwe Rozen B.V., De Kwakel (NL)

( * ) Notice: Subject to any disclaimer, the term of this patent is extended or adjusted under 35 U.S.C. 154(b) by 0 days.

(21) Appl. No.: 09/480,595

(22) Filed: Jan. 10, 2000

(51) Int. Cl.[7] ..... A01H 5/00
(52) U.S. Cl. ..... Plt./122
(58) Field of Search ..... Plt./122

(56) References Cited

U.S. PATENT DOCUMENTS

PP7,540 P * 6/1991 Nielson ..... Plt./122
PP8,242 P * 6/1993 Meilland ..... Plt./122
PP8,349 P * 8/1993 Ilsink ..... Plt./122
PP9,483 P * 3/1996 Oleson ..... Plt./122
PP9,628 P * 8/1996 Saville ..... Plt./122
PP9,973 P * 7/1997 Meilland ..... Plt./122
PP11,383 P * 5/2000 Walden ..... Plt./122
PP11,541 P * 10/2000 Oleson ..... Plt./122
PP11,543 P * 10/2000 Oleson ..... Plt./122

OTHER PUBLICATIONS

UPOV–ROM GTITM Computer Database, Feb. 2001, GTI Jouve Retrieval Software, citation for 'Ruiskjol'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinctive cultivar of miniature rose plant named 'Ruiskjol', characterized by its glossy dark green leaves; large double scarlet red-colored flowers; and excellent post-production longevity.

1 Drawing Sheet

BACKGROUND OF THE INVENTION

The present invention relates to a new and distinct cultivar of the miniature rose class, botanically known as *Rosa hybrida*, and hereinafter referred to by the cultivar name Ruiskjol.

The new miniature rose is a naturally-occurring whole plant mutation of the commercial *Rosa hybrida* cultivar Ruimats, disclosed in U.S. Plant Pat. No. 10,820. The new minature rose was discovered and selected by the Inventor in a greenhouse in Hazerswoude, The Netherlands. Plants of the new miniature rose differ from plants of the parent cultivar primarily in flower color as plants of the cultivar Ruimats have dark orange-colored flowers.

Asexual reproduction of the new cultivar by cuttings taken at Hazerswoude, The Netherlands, has shown that the unique features of this new miniature rose plant are stable and reproduced true to type in successive generations of asexual reproduction.

SUMMARY OF THE INVENTION

The following traits have been repeatedly observed and are determined to be the unique characteristics of 'Ruiskjol'. These characteristics in combination distinguish the new miniature rose plant as a new and distinct cultivar:

1. Glossy dark green leaves.
2. Large double scarlet red-colored flowers.
3. Excellent postproduction longevity.

The new miniature rose plant has not been observed under all possible environmental conditions. The phenotype may vary significantly with variations in environment such as temperature and light level, without, however, any variance in genotype.

BRIEF DESCRIPTION OF PHOTOGRAPH

The accompanying colored photograph illustrates typical plants of the new miniature rose plant, showing the colors as true as it is reasonably possible to obtain in colored reproductions of this type. Colors in the photograph may differ slightly from the color values cited in the detailed botanical description which more accurately describe the actual colors of the new miniature rose. The photograph comprises a top perspective view of a large container of multiple plants of the new miniature rose grown in Keller, Tex.

DETAILED BOTANICAL DESCRIPTION

The following observations and measurements describe plants grown in Keller, Tex., in 15-cm containers under conditions which closely approximate commercial outdoor production conditions during the summer and early autumn. Plants used for the description were about 15 weeks old.

In the following description, color references are made to The Royal Horticultural Society Colour Chart except where general terms of ordinary dictionary significance are used.

Classification:
*Botanical.*—*Rosa hybrida* cultivar Ruiskjol.
*Commercial.*—Miniature pot rose.

Parentage: Naturally-occurring whole plant mutation of *Rosa hybrida*, disclosed in U.S. Plant Pat. No. 10,820.

Propagation:
*Type.*—Terminal or stem cuttings.
*Time to rooting.*—8 to 10 days with soil temperatures of 20° C.
*Root description.*—Propagates easily, roots strong and well-branched.

Plant description:

*Form.*—Mostly upright; somewhat open.

*Plant height.*—About 35 cm.

*Plant width.*—About 28 cm.

*Growth habit.*—Vigorous. Suitable for 10-cm and larger containers.

*Crop time.*—Time to produce a finished plant in a 10-cm container 20 to 30 cm in height and 15 to 20 cm in width is generally about 10 to 12 weeks depending on average temperature, light level, and cultural practices.

*Stem and lateral branches.*—Branching habit: Freely; branches will potentially form at every node. Diameter of lateral branches, at base: About 4 mm. Internode length: About 2.1 cm. Texture: Glabrous. Color: 144A or slightly darker. Prickles: Length: About 4 mm. Color: Light brown.

*Foliage description.*—Leaves arranged alternately, compound with typically three to seven leaflets per leaf, generally symmetrical, abundant, and flat to slightly concave in aspect. Stipules at petiole base; stipules about 6 mm in length. Leaflet length: About 2.4 cm. Leaflet width: About 1.5 cm. Shape: Ovate. Apex: Acute. Base: Obtuse. Margin: Serrate. Texture, both surfaces: Glabrous, leathery. Venation pattern: Pinnate. Petiole length: About 1.7 cm to base of lower leaflet; about 3.4 cm to base of terminal leaflet. Petiole diameter: About 1 mm. Petiole texture: Smooth. Color: Young foliage, upper surface: Close to 146A. Young foliage, lower surface: Close to 146B to 146C. Mature foliage, upper surface: Close to 146A to 147A; reddish, 59A, overtones towards and at margins. Mature foliage, lower surface: Close to 146B to 147B. Venation, both surfaces: Similar to ground color. Petiole: Upper surface, close to 59A; lower surface, 146B.

Flower description:

*Flower type and habit.*—Large double scarlet red flowers. Consistently symmetrical rosette flowers that are relatively flat in shape. Freely and continuously flowering. The flowers are borne singly on peduncles or arranged in large sprays with about two or three flowers per spray. Flower persistent.

*Flowering season.*—Year-round under greenhouse conditions, optimal flowering from spring through autumn under garden conditions.

*Flower diameter.*—About 3.6 cm.

*Flower depth (height).*—About 2.1 cm.

*Flower longevity on plant.*—About 12 to 14 days.

*Fragrance.*—Very faint, typical of Rosa.

*Flower buds (stage of showing color).*—Shape: Ovoid. Length: About 1.1 cm. Diameter: About 8 mm. Color: Close to 46A.

*Petals.*—Quantity: About 36 per flower; typically about seven rows. Length, outer petals: About 1.7 cm. Width, outer petals: About 1.8 cm. Shape: Roughly cordate. Apex: Cuspidate. Base: Acute. Margin: Entire. Texture: Smooth, velvety. Color: When opening, upper surface: 46A; base, white. When opening, lower surface: 46B; base, white. Fully opened, upper surface: 45A to 46A; flower color resists fading with subsequent development; base, white. Fully opened, lower surface: 46B to 46C; base, white.

*Sepals.*—Quantity: Typically five per flower. Length: About 1.9 cm. Diameter: About 5 mm. Shape: Narrowly ovate with sharply acute foliaceous appendages. Apex: Sharply pointed. Base: Truncate. Texture: Pubescent, fine white hairs on upper surface. Color: Upper surface; 146A; covered with fine white hairs. Lower surface: 146A.

*Peduncles.*—Strength: Good yet flexible. Aspect: Erect. Length: About 3.2 cm. Color: 146A with red, close to 59A, overtones.

*Reproductive organs.*—Stamens: Quantity: About 42 per flower. Anther size: About 1.5 by 1 mm. Anther shape: Bilobate. Anther color: Close to 4A. Pistils: Quantity: About 18 per flower. Style length: About 3.5 mm. Style color: Close to 4A.

*Seed.*—Seed production has not been observed.

Disease resistance: Plants of the new miniature rose have not been shown to be resistant to Powdery Mildew.

Temperature tolerance: Plants of the new miniature rose have been shown to be tolerate to temperatures ranging from 0 to 45° C.

It is claimed:

1. A new and distinct miniature rose plant named 'Ruiskjol', as illustrated and described.

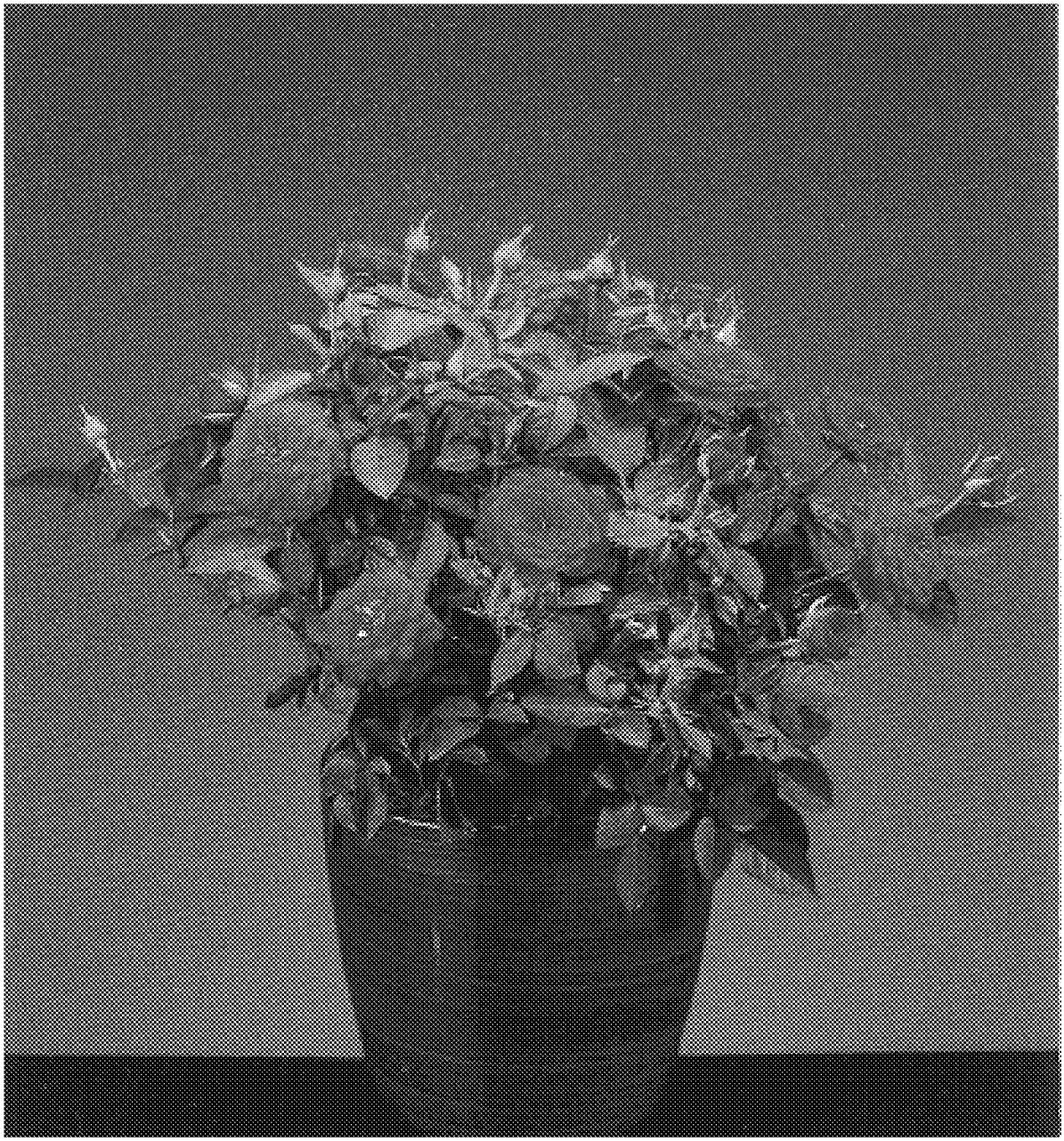

* * * * *